(12) United States Patent
Wang (10) Patent No.: US 10,676,407 B2
(45) Date of Patent: Jun. 9, 2020

(54) INCLINED REACTOR OF BOTTOM GAS-INLET TYPE FOR AEROBIC FERMENTATION AND METHOD FOR AEROBIC FERMENTATION

(71) Applicant: Hunan Sakal Environmental Science and Technology Co., Ltd., Changsha (CN)

(72) Inventor: Shen Wang, Changsha (CN)

( * ) Notice: Subject to any disclaimer, the term of this patent is extended or adjusted under 35 U.S.C. 154(b) by 105 days.

(21) Appl. No.: 15/494,517

(22) Filed: Apr. 23, 2017

(65) Prior Publication Data
US 2017/0226023 A1 Aug. 10, 2017

Related U.S. Application Data

(63) Continuation of application No. PCT/CN2014/090219, filed on Nov. 4, 2014.

(30) Foreign Application Priority Data

Oct. 23, 2014 (CN) .......................... 2014 1 0567951

(51) Int. Cl.
*C12M 1/00* (2006.01)
*C12M 1/02* (2006.01)
(Continued)

(52) U.S. Cl.
CPC .............. *C05F 17/964* (2020.01); *C05F 9/02* (2013.01); *C05F 17/00* (2013.01); *C05F 17/20* (2020.01); *C05F 17/60* (2020.01); *C05F 17/70* (2020.01); *C05F 17/90* (2020.01); *C05F 17/929* (2020.01); *C05F 17/979* (2020.01);
(Continued)

(58) Field of Classification Search
CPC ........ C05F 17/00; C05F 17/02; C05F 17/027; C05F 17/0023; C05F 17/0063; C05F 17/0036; C05F 17/0072; C05F 17/0258; C05F 17/0282; C05F 9/02; C12M 23/02; C12M 27/06; C12M 29/04; C12M 29/14; C12M 41/12; C12M 41/20; C12M 41/22; C12M 41/34; C12M 41/40; C12M 41/42;
(Continued)

(56) References Cited

FOREIGN PATENT DOCUMENTS

KR 20100121833 A * 11/2010

OTHER PUBLICATIONS

You Jong Han et al., "English machine translation of document KR-10-2010-0121833-A" (Year: 2010).*

* cited by examiner

*Primary Examiner* — Liban M Hassan
(74) *Attorney, Agent, or Firm* — Erson IP (Nelson IP)

(57) ABSTRACT

The present application provides a reactor with an inclined bottom gas-inlet for aerobic fermentation. A fermenter is provided with a circular inner tank, end covers and a jacket. An airtight fermentation space is formed in the fermenter by the inner tank, an upper end cover and a lower end cover. A feed opening and an exhaust outlet are arranged at an upper part of the fermenter, and a discharge opening is arranged at a lower part of the lower end cover of the fermenter. An energy-saving stirrer is mounted in the fermenter. A plurality of air chambers are arranged at an external wall at the bottom of the inner tank of the fermenter and are within the jacket. A plurality of aeration nozzles are defined on an inner side of each air chamber, and the aeration nozzles are disposed next to the inner tank.

7 Claims, 8 Drawing Sheets

(51) Int. Cl.
    *C12M 1/34*         (2006.01)
    *C05F 17/02*        (2006.01)
    *C05F 17/964*      (2020.01)
    *C05F 17/00*        (2020.01)
    *C05F 17/20*        (2020.01)
    *C05F 17/60*        (2020.01)
    *C05F 17/70*        (2020.01)
    *C05F 17/90*        (2020.01)
    *C05F 17/929*      (2020.01)
    *C05F 17/979*      (2020.01)
    *C05F 17/993*      (2020.01)
    *C05F 9/02*         (2006.01)
    *C12M 1/06*        (2006.01)
    *C12M 1/36*        (2006.01)
    *C12P 39/00*       (2006.01)

(52) U.S. Cl.
    CPC ........... *C05F 17/993* (2020.01); *C12M 23/02* (2013.01); *C12M 27/06* (2013.01); *C12M 29/04* (2013.01); *C12M 29/14* (2013.01); *C12M 29/20* (2013.01); *C12M 41/12* (2013.01); *C12M 41/20* (2013.01); *C12M 41/22* (2013.01); *C12M 41/34* (2013.01); *C12M 41/40* (2013.01); *C12M 41/42* (2013.01); *C12M 41/48* (2013.01); *C12M 47/18* (2013.01); *C12P 39/00* (2013.01); *Y02P 20/145* (2015.11); *Y02W 30/43* (2015.05)

(58) Field of Classification Search
    CPC ........ C12M 41/48; C12M 47/18; C12P 39/00; Y02P 20/145; Y02W 30/43
    USPC ...................................... 435/300.1
    See application file for complete search history.

INCLINED REACTOR OF BOTTOM GAS-INLET TYPE FOR AEROBIC FERMENTATION AND METHOD FOR AEROBIC FERMENTATION

CROSS-REFERENCE TO RELATED APPLICATIONS

This application is a continuation of International Patent Application No. PCT/CN2014/090219 with an international filing date of Nov. 4, 2014, designating the United States, and further claims priority benefits to Chinese Patent Application No. 201410567951.7 filed Oct. 23, 2014. The contents of all of the aforementioned applications, including any intervening amendments thereto, are incorporated herein by reference.

FIELD OF THE INVENTION

The present application relates to the field of bio-fermentation, and more particularly relates to a reaction system and method for aerobic fermentation, which is used for harmless and recycling treatment of organic wastes.

BACKGROUND OF THE INVENTION

The annual yield of organic wastes, including human and animal excreta, food wastes, sludge from sewage treatment plants, rotten fruits and vegetables from fruit and vegetable markets and the like, is 10 times of the annual yield of industrial solid wastes. The organic wastes are of large amount and high concentration, which will bring severe environmental pollution if they are not treated in time.

Composting treatment (aerobic fermentation) of organic wastes can achieve recycling utilization of wastes, which is hence widely applied. Various aerobic fermentation reactors have been designed to improve the efficiency of aerobic fermentation, and decrease manufacturing costs of the fermentation devices and operating costs.

The existing aerobic fermentation devices are mainly horizontal type or vertical type. Chinese patent No. CN 1100024 C discloses a horizontal-type aerobic fermentation reactor with a horizontal-slot structure. The reactor and materials to be fermented are heated by hot oil. The materials to be fermented are stirred by mixing blades so as to realize pile turning and oxygen supply. However, an upper surface of this reactor is too large to insulate heat, and hence the energy consumption is very huge. The materials to be fermented will easily produce fouling on the inner wall of the fermenter, which makes it difficult for the hot oil to conduct heat. The fouling may be reduced by increasing the number of mixing blades, however too much mixing blades may increase energy consumption. Moreover, in this Chinese patent, it is hard for fermented products to be discharged, since the mixing blades are helpless for discharging, and hence the fermented products are manually discharged.

Chinese patent No. 95119800.9 discloses a horizontal aerobic fermentation reactor with a horizontal-slot structure. The reactor and materials to be fermented are heated by an electrical heater. The materials to be fermented are stirred by screw wing so as to realize pile turning and oxygen supply. However, an upper surface of this reactor is too large to insulate heat. The materials to be fermented are easily compacted by spiral rotation, the air in materials is hence forced out causing anaerobic reaction in which toxic gases such as hydrogen sulfide may be generated, and the aerobic reaction is endangered. The energy consumption for switching between positive and negative directions of spiral rotation is very large, and the device is easily broken down. Moreover, the fermented products are manually discharged under poor dirty working condition.

Chinese patent No. CN 102757270 B discloses a horizontal aerobic fermentation reactor with a horizontal rolling structure. This reactor solves the problems of heating, heat preservation, air intake and outtake, material feed and discharge, and so on. However, its disadvantage is that the materials to be fermented are easily produced fouling on the inner wall of the fermenter, which affects heat conduction.

Chinese utility model No. CN 201933029 U discloses a vertical aerobic fermentation reactor. The materials to be fermented in a lower part of the reactor are easily compacted by the materials in an upper part of the reactor, which makes it hard for the materials to be fermented in the lower part to contact with air. Accordingly, the fermentation is non-uniform, which easily causes anaerobic reaction to produce toxic gases such as hydrogen sulfide.

Chinese patent No. 03821392.3 discloses a vertical aerobic fermentation reactor. In this invention, the problem that the materials in the lower part are compacted is well solved by providing a processing area in the vertical composting device. However, this device is big and tall, the energy consumption for turning over the materials in the processing area is huge, and the manufacturing and operational costs are very expensive.

SUMMARY OF THE INVENTION

Aiming at above defects in the prior art, the objective of the present application is to provide an inclined reactor of bottom gas-inlet type with heat conduction for aerobic fermentation and a method for aerobic fermentation, and the reactor has the advantages of small footprint, being uninfluenced by the factors of environment and low temperature, high fermentation efficiency, no fouling produced on the inner part of the reactor, easy discharge, easy collection of exhaust gases, no secondary pollution produced, low moisture content of finished products, harmless and recycling treatment of organic wastes, and good environmental protection effect.

The technical solutions of the present application for solving the technical problems are as follows:

In one aspect, an inclined reactor of bottom gas-inlet type for aerobic fermentation is provided. A fermenter is provided with a circular inner tank, end covers and a jacket; an airtight fermentation space is formed in the fermenter by the inner tank, an upper end cover and a lower end cover; a feed opening and an exhaust outlet are arranged at an upper part of the fermenter, and a discharge opening is arranged at a lower part of the lower end cover of the fermenter; a length of the fermenter is greater than or equal to a diameter of the fermenter; the fermenter is fixed on a base having a height difference and is hence in an inclined state; an energy-saving stirrer is mounted in the fermenter, and the energy-saving stirrer is formed by connecting several groups of tangential plates or a spiral combination of tangential plates, a radial rod, a stirring rod and a stirring shaft; several groups of air chambers are arranged at an external wall at the bottom of the inner tank of the fermenter, the air chambers are arranged inside the jacket, several aeration nozzles are defined on an inner side of each air chamber, and the aeration nozzles are close to the inner tank.

Advantageously, the number of the radial rod of the energy-saving stirrer is multiple, a distance between an end of each radial rod and a center of the stirring shaft is the same, and radial rods are radially fixed to the stirring shaft and are uniformly arranged around the stirring shaft; the number of the stirring rod is multiple, and stirring rods are fixed to the radial rods; and the tangential plates or the spiral combination of the tangential plates are fixedly connected to ends of the radial rods.

Advantageously, the energy-saving stirrer is provided with two structures; in one structure, the radial rod is fixed to the stirring shaft, the stirring rod is fixed to the radial rod, the tangential plates are fixed to an end of the radial rod, and hence the energy-saving stirrer used for wall-sticking fermentation materials is formed; in the other structure, the radial rod is fixed to the stirring shaft, the stirring rod is fixed to the radial rod, the tangential plates firstly fixed to the spiral combination are then fixed to an end of the radial rod, and hence the energy-saving stirrer with the functions of wall sticking proof and spiral transmission is formed.

Advantageously, two ends of the energy-saving stirrer are respectively supported on bearings of two end covers, a motor/reducer is mounted at a driving end of the energy-saving stirrer, and the motor/reducer drives the energy-saving stirrer to rotate.

Advantageously, a feed valve is arranged for the feed opening at the upper part of the fermenter; the feed valve comprises a manual valve and an automatic valve; a heat insulating material is wrapped around the fermenter; a heat conductive medium-inlet flange and a heat conductive medium-outlet flange are respectively arranged at a lower part and an upper part of the jacket of the fermenter, and are respectively connected to an inlet and an outlet of heat conductive medium-circulating pipes to form a heat circulating loop.

Advantageously, the air chambers are connected to a gas valve and a high-pressure gas source via a gas inlet pipe, the high-pressure gas entering into the air chambers is firstly heated by the heat conductive medium circulated in the jacket, then enters into the fermenter via the aeration nozzles, and is hence thoroughly mixed with materials to be fermented.

Advantageously, the exhaust outlet at the upper part of the upper end cover of the fermenter in the inclined state is connected to an exhaust fan via pipes, the exhaust fan is connected to a bio-deodorization filter tower via the pipes, and exhaust gas is filtered by the bio-deodorization filter tower before being exhausted; a temperature sensor and an oxygen sensor are respectively arranged at two ends of the discharge opening of the lower end cover; outputs of the temperature sensor and the oxygen sensor are respectively connected to corresponding inputs of a controller, the controller is configured to compare input values from the sensors with preset values, and outputs of the controller are connected to a circulating pump, a heat source boiler, the energy-saving stirrer, an exhaust fan, a gas valve and a high-pressure gas source; the controller is also capable of setting a preset timing to start and stop the circulating pump, the heat source boiler, the energy-saving stirrer, the exhaust fan, the gas valve and the high-pressure gas source without using the sensors.

Advantageously, a distance between the tangential plates or the spiral combination of the tangential plates and an inner wall of the fermenter is in range of 1-5 cm.

Advantageously, the radial rod is in a lamellar structure, lengths of blades in the lamellar structure are the same, a width of the lamellar structure is significantly greater than a thickness of the lamellar structure; the stirring rod is in a cylindrical shape, cuboid shape or lamellar shape; if the stirring rod is in the cuboid or lamellar shape, a width of the stirring rod is greater than a thickness of the stirring rod; the tangential plates are in a cylindrical shape, cuboid shape or lamellar shape; if the tangential plates are in the cuboid or lamellar shape, a width of each tangential plate is greater than a thickness of the tangential plate.

In another aspect, a method for aerobic fermentation is provided, which comprises:

(1) designing and manufacturing an inclined reactor of bottom gas-inlet type for aerobic fermentation, wherein a fermenter is provided with a circular inner tank, end covers and a jacket; an airtight fermentation space is formed in the fermenter by the inner tank, an upper end cover and a lower end cover; a feed opening and an exhaust outlet are arranged at an upper part of the fermenter, and a discharge opening is arranged at a lower part of the lower end cover of the fermenter; a length of the fermenter is greater than or equal to a diameter of the fermenter; the fermenter is fixed on a base having a height difference and is hence in an inclined state; an energy-saving stirrer is mounted in the fermenter, and the energy-saving stirrer is formed by connecting several groups of tangential plates or a spiral combination of tangential plates, a radial rod, a stirring rod and a stirring shaft; several groups of air chambers are arranged at an external wall at the bottom of the inner tank of the fermenter, the air chambers are arranged inside the jacket, several aeration nozzles are defined on an inner side of each air chamber, and the aeration nozzles are close to the inner tank; the number of the radial rod of the energy-saving stirrer is multiple, a distance between an end of each radial rod and a center of the stirring shaft is the same, and radial rods are radially fixed to the stirring shaft and are uniformly arranged around the stirring shaft; the number of the stirring rod is multiple, and stirring rods are fixed to the radial rods; and the tangential plates or the spiral combination of the tangential plates are fixedly connected to ends of the radial rods; a feed valve is arranged for the feed opening at the upper part of the fermenter; the feed valve comprises a manual valve and an automatic valve; a heat insulating material is wrapped around the fermenter a heat conductive medium-inlet flange and a heat conductive medium-outlet flange are respectively arranged at a lower part and an upper part of the jacket of the fermenter, and are respectively connected to an inlet and an outlet of heat conductive medium-circulating pipes to form a heat circulating loop; the air chambers are connected to a gas valve and a high-pressure gas source via a gas inlet pipe, the high-pressure gas entering into the air chambers is firstly heated by the heat conductive medium circulated in the jacket, then enters into the fermenter via the aeration nozzles, and is hence thoroughly mixed with materials to be fermented;

(2) starting devices, wherein a main power source is closed to delivery electric power to the devices, start buttons of the devices are pressed, a controller controls to start a circulating pump and a heat source boiler sequentially; heat conductive medium heated by the heat source boiler in a heating system enters into the reactor for aerobic fermentation under the action of the circulating pump via a heat conductive medium-inlet flange so as to heat the inner tank of the reactor for aerobic fermentation;

(3) feeding raw materials, wherein a feeding button is pressed, the controller controls to start a transmission device, moderate organic wastes under pre-treatment and aerobic bacteria are transmitted into the reactor for aerobic fermentation via the transmission device; the controller controls the energy-saving stirrer to rotate when the transmission device starts; after finishing feeding raw materials, the controller controls the transmission device and the energy-saving stirrer to stop, and controls a feed valve to close so as to prevent odor from spilling via the feed opening;

(4) aeration and fermentation, wherein after the feed valve is closed, the controller controls the heating system to heat materials to a preset temperature that is suitable for aerobic fermentation; the controller controls a high-pressure gas source/gas valve to start, and controls the energy-saving stirrer to rotate; air from the high-pressure gas source enters into air chambers via a gas inlet pipe, and is firstly heated by circulating heat conductive medium in the jacket, then enters into the fermenter via aeration nozzles, contacts with materials to be fermented and supplies oxygen to the materials;

(5) exhaust gas treatment, wherein when the controller controls the high-pressure gas source/gas valve to start, the controller controls an exhaust fan connected to an exhaust outlet to start, the exhaust fan transmits the fermentation exhaust gas to a bio-deodorization filter tower via pipes, and exhaust gas is filtered by the bio-deodorization filter tower before being exhausted;

(6) time-delay controlling, wherein the high-pressure gas source/gas valve and the energy-saving stirrer are stopped by adopting time delay; when a preset time delay set by the controller ends, the controller automatically closes the high-pressure gas source/gas valve, closes the exhaust fan under a time delay, and automatically controls the energy-saving stirrer stop rotating;

(7) automatically adjusting fermentation conditions, wherein the controller controls outputs of the high-pressure gas source according to feedback of an oxygen sensor; if the controller determines that oxygen level detected by the oxygen sensor is smaller than a preset lower limit value, the controller controls to open the gas valve and the high-pressure gas source, compressed air enters into the fermenter from the aeration nozzles of the air chambers at a bottom of the fermenter via a gas inlet pipe, diffuses upwards, and is thoroughly mixed with materials to be fermented; if the controller determines that the oxygen level detected by the oxygen sensor is greater than a preset upper limit value, the controller controls to close the high-pressure gas source; the controller is also capable of setting a timing to open and close the gas valve and the high-pressure gas source, and oxygen supplying for fermentation is still ensured without the oxygen sensor;

the controller controls the energy-saving stirrer to act according to feedback of a temperature sensor; if the controller determines that temperature detected by the temperature sensor is higher than a preset temperature, the controller controls a motor/reducer to start so as to drive the energy-saving stirrer to rotate; stirring time of the energy-saving stirrer is controlled by the controller, the controller is also capable of setting a timing to start and stop the motor/reducer so as to turn over the materials periodically;

(8) adjusting temperature of the heating system, wherein the controller controls the circulating pump and heat source boiler to start and stop according to feedback of the temperature sensor; if temperature detected by the temperature sensor is lower than a preset value, the circulating pump is started, and the boiler is started after a time delay of t1; if the temperature detected by the temperature sensor is higher than a preset value, the controller controls the heat source boiler stop operating, and controls the circulating pump stop operating after a time delay of t2; values of t1 and t2 are determined by inertia of the system, which can be determined and adjusted in operation site;

(9) discharging materials, wherein when a preset fermentation time ends, the controller controls to open a discharging gate and controls the energy-saving stirrer to reverse so as to discharge materials that have been fermented, and the materials that have been fermented are transmitted to a next procedure via an external transmission device;

(10) the controller controlling to close the discharge opening after finishing discharging the materials, the external transmission device being started again to transmit moderate raw materials to be fermented into the inclined reactor of bottom gas-inlet type for aerobic fermentation, and remaining stale acting as yeast to inoculate and ferment raw materials newly added;

(11) repeating above steps so as to ensure bio-fermentation degradation reaction of organic wastes to circulate with a high speed;

(12) after finishing all above steps, the controller switching off power supply of the high-pressure gas source and the heat source boiler, closing the gas valve and the feed valve.

Advantageous Effects

Compared with the prior art, the advantageous effects of the present invention is that physical conditions for aerobic fermentation is sufficiently created, which ensures the fermentation reaction to take place with a high speed under constant temperature and enough oxygen.

According to the structure, function of the tangential plates and the distance between the tangential plates and the inner wall of the fermenter, it is designed that the tangential plates are fixed to the end of the radial rod to form the energy-saving stirrer used for wall-sticking fermentation materials; further, according to the material transmission function of the spiral combination, it is designed that the tangential plates firstly fixed to the spiral combination are then fixed to an end of the radial rod to form the energy-saving stirrer with the functions of wall sticking proof and spiral transmission, and it is fully functioned.

Fresh air entering into the air chambers via the gas inlet pipe is firstly heated by the heat conductive medium circulated in the jacket, and then enters into the fermenter, which hence will not make the fermentation temperature to fluctuate. The bottom gas inlet mode is more uniform, and no dead angle of hypoxia will be generated in coordination with stirring. The start of the stirrer is related to the fermentation temperature, and the start times are significantly decreased which is helpful to energy saving.

The odor is centrally collected and filtered by the bio-deodorization filter tower before being exhausted, which makes the gases such as ammonia gas and nitrogen gas to be recycled, instead of being discharged into the air to pollute environmental.

The device of the present invention is of small footprint, uninfluenced by the factors of environment and low temperature, high fermentation efficiency, no secondary pollution produced since the aerobic fermentation is carried out in the airtight tank, low moisture content of finished products since the forced ventilation takes away moisture without affecting the fermentation effect and efficiency, harmless and recycling treatment of organic wastes, and good environmental protection effect.

A key technical character of the present invention is that the fermenter is inclined, which is helpful to automatically discharge materials by the gravity of the materials and avoids the materials to be compacted due to high pressure at the discharge end when discharging by spiral rotation at the discharge end. The anaerobic reaction will take place if the materials are compacted, and hence the toxic gases such as hydrogen sulfide will be produced. Energy consumption for switching between positive and negative directions of spiral rotation is huge, and the device is easily broken down. The inclined fermenter of the present invention overcomes above disadvantages of horizontal aerobic fermentation reactor and vertical aerobic fermentation reactor, and has unique advantages.

Another key technical character of the present invention is that air chambers and aeration nozzles defined at the lower part of the fermenter are connected to the high-pressure gas source. In this way, the air entering into the fermenter is heated, which avoids temperature fluctuation of the materials in the fermenter to affect the fermentation efficiency. Moreover, the aeration nozzles aerate air upwards from the lower part of the materials in the fermenter, which overcomes the defect in the prior art that it is hard for the air entering into the fermenter from an end of the fermenter to enter into the materials. In the present invention, a plurality of aeration nozzles is provided at the lower part, which is helpful to mix with the materials and promotes the fermentation reaction.

Another key technical character of the present invention is that the radial rod is mounted to the stirring shaft, the stirring rod is mounted to the radial rod, and the tangential plates are mounted to the end of the radial rod, so as to form the energy-saving stirrer. The stirring resistance is small, the materials will be stirred radially and axially, the tangential plates are capable of avoiding the materials sticking to the inner wall of the fermenter to form fouling, and the radial rod and stirring rod are capable of stirring and loosening the materials all round, which overcomes the defects in the prior art of single technique, large resistance for turning over the materials, large energy consumption and easy compaction to the materials. Accordingly, the present invention has a plurality of technical characters with inventive step, and the technical effects are significant.

Wherein in the drawings:
01—exhaust outlet, 02—upper end cover, 03—first bearing, 04—motor/reducer, 05—torque arm, 06—torque arm fixing base, 07—inlet flange, 08—outlet flange, 09—fermentation reactor base, 10—first pin shaft, 11—gas inlet pipe, 12—second pin shaft, 13—tank body supporting hinged base, 14—discharge opening, 15—lower end cover, 16—second bearing, 17—energy-saving stirrer, 18—fermenter barrel, 19—feed valve, 20—feed opening, 21—feed opening funnel, 201—stirring shaft, 202—radial rod, 203—stirring rod, 204—tangential plate, 205—spiral combination, 301—hot water passage, 302—air chamber, 303—aeration nozzle, 304—jacket, 305—inner tank, 306—heat insulating material, 401—heat source boiler, 402—pipeline, 403—high-pressure gas source, 404—gas tank, 405—gas valve, 406—exhaust fan, 407—bio-deodorization tower, 408—circulating pump, 409—controller, 410—temperature sensor, 411—oxygen sensor, 412—transmission device.

DETAILED DESCRIPTION OF THE PREFERRED EMBODIMENT

The present invention will be further described with reference to the accompanying drawings.

As shown in the figures, one technical solution provided in the present invention is: an inclined reactor of bottom gas-inlet type for aerobic fermentation. The fermenter fixed on a base 09 having a height difference is in an inclined state. The fermenter is provided with a circular inner tank 305, end covers and a jacket 304. An airtight fermentation space is formed in the fermenter by the inner tank 305, an upper end cover 02 and a lower end cover 15. A length of the fermenter is greater than or equal to a diameter of the fermenter. A heat insulating material 306 is wrapped around the fermenter.

A feed opening 20, a feed valve 19 and a feed opening funnel 21 are arranged at an upper part of the fermenter, from which materials to be fermented enter into the fermenter. An exhaust outlet 01 is arranged at an upper part of the upper end cover 02, from which the waste gases are drawn by an exhaust fan. A discharge opening 14 with a hatch door is arranged at a lower part of the lower end cover 15, from which the fermented materials are discharged.

An energy-saving stirrer 17 is mounted in the fermenter, which is formed by connecting several groups of tangential plates 204 or a spiral combination 205 of tangential plates 204, a radial rod 202, a stirring rod 203 and a stirring shaft 201. The stirring rod 203 and the radial rod 202 are uniformly arranged on the stirring shaft 201 in a structure of spiral curved array. The tangential plates 204 or the spiral combination 205 of tangential plates 204 are fixed to an end of the radial rod 202. Two ends of the energy-saving stirrer 17 are respectively supported by bearings fixed to the upper end cover 02 and lower end cover 15, which ensures the energy-saving stirrer 17 to move in a circle, instead of moving along an axial line. A motor/reducer 04 is mounted at a driving end of the energy-saving stirrer 17, which drives the energy-saving stirrer 17 to move in a circle.

The feed valve 19 is arranged at the feed opening 20. The feed valve 19 is closed after finishing feed, which prevents the odor overflowing from the feed opening 20 during the fermentation.

A heat conductive medium-inlet flange 07 and a heat conductive medium-outlet flange 08 are respectively arranged at a lower part and an upper part of the jacket of 304 the fermenter, and are respectively connected to an inlet and an outlet of heat conductive medium-circulating pipes. An outlet of a heat source boiler is connected to the heat conductive medium-inlet flange 07 arranged at the lower part of the fermenter via a pump, and the heat conductive medium-outlet flange 08 arranged at the upper part of the fermenter is connected to an inlet of the heat source boiler to form a heat circulating loop. The heat conductive medium comprises but not limited to hot water, heat conductive oil, or steam.

Several groups of air chambers 302 are welded to an external wall at the bottom of the inner tank of the fermenter. The air chambers 302 are arranged inside the jacket 305.

Several aeration nozzles 303 are defined on an inner side of each air chamber 302, and the aeration nozzles 303 are close to the inner tank 305. The air chambers 302 are connected to a high-pressure gas source 403 and a gas valve 405 via a gas inlet pipe 11. The air from the high-pressure gas source 403 (including but not limited to an air compressor or a wind turbine) is firstly heated by the heat conductive medium circulated in the jacket 304, then enters into the fermenter via the aeration nozzles 303, and is hence thoroughly mixed with materials to be fermented.

The exhaust outlet 01 at the upper part of the upper end cover 02 is connected to an exhaust fan 406 via pipes. The exhaust fan 406 draws the exhaust gases and blows it to a bio-deodorization filter tower 407, and exhaust gases are filtered by the bio-deodorization filter tower before being exhausted.

A temperature sensor 410 and an oxygen sensor 411 are respectively arranged at two ends of the discharge opening 14 of the lower end cover 15, which are used for detecting reaction conditions in the fermenter. Outputs of the temperature sensor 410 and the oxygen sensor 411 are respectively connected to corresponding inputs of a controller 409. The controller 409 is configured to compare input values from the sensors with preset values. Outputs of the controller are capable of controlling start and stop of the heat source boiler 401, the energy-saving stirrer 17 and the exhaust fan 17. The controller is also capable of setting a preset timing to start and stop the energy-saving stirrer 17 and the exhaust fan 406. When the temperature reaches a preset value, the controller 409 may control to stop the heat source boiler 401 and stop a circulating pump 408 after a time delay.

Figure 1:
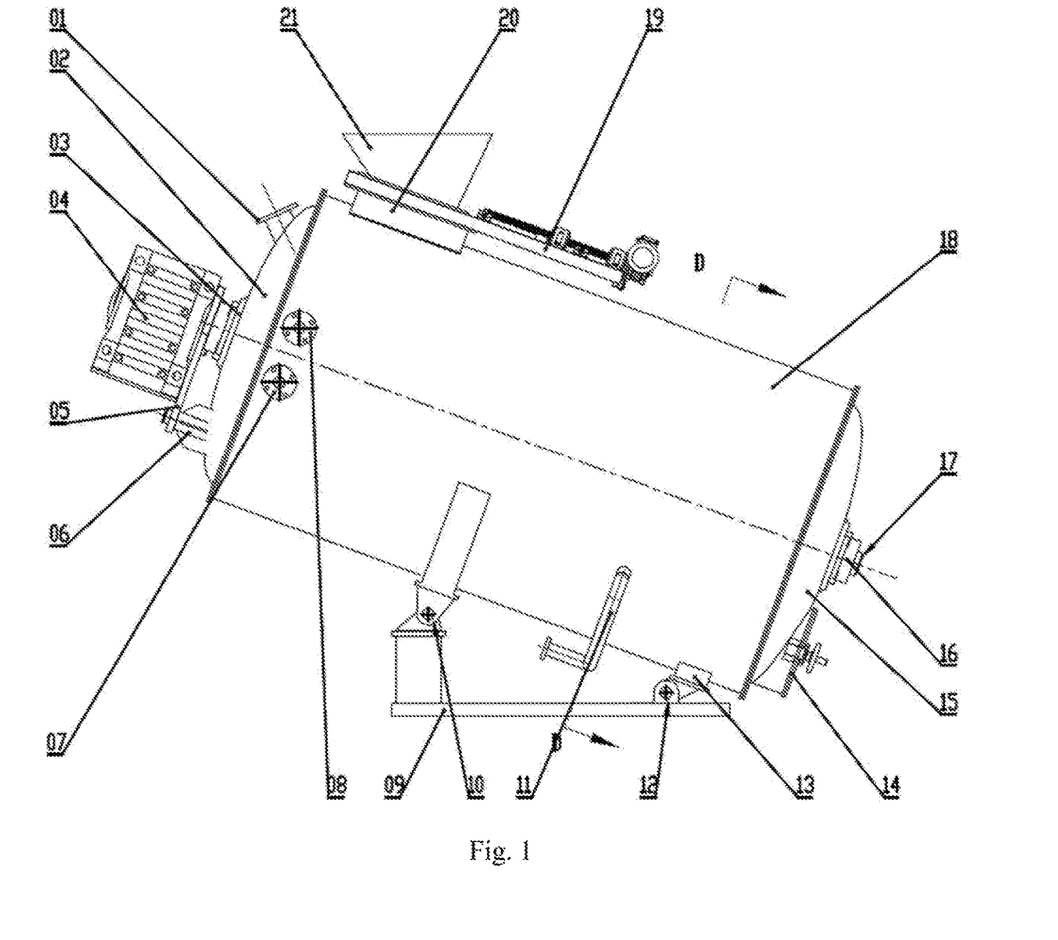
FIG. 1 is front view of an inclined aerobic fermentation reactor.
Figure 2:
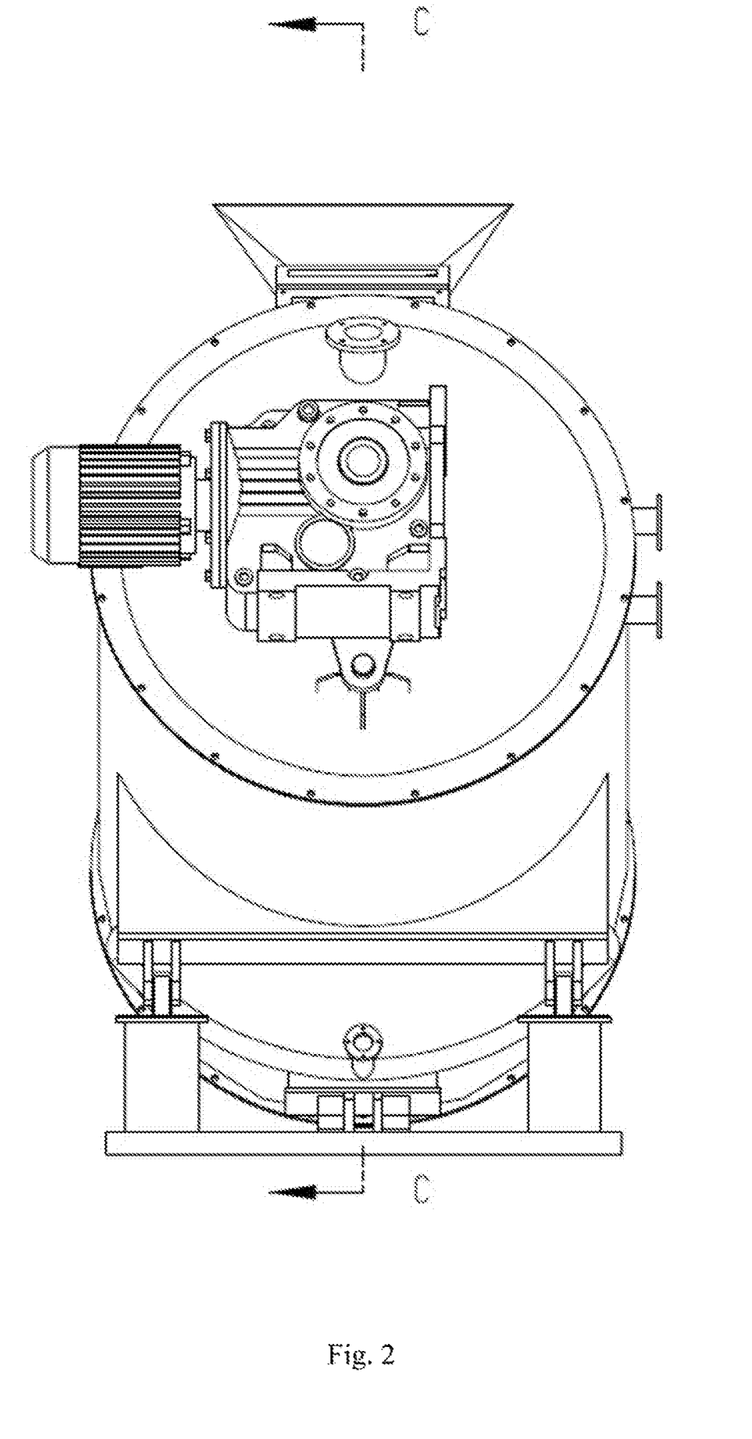
FIG. 2 is left view of the inclined aerobic fermentation reactor.
Figure 3:
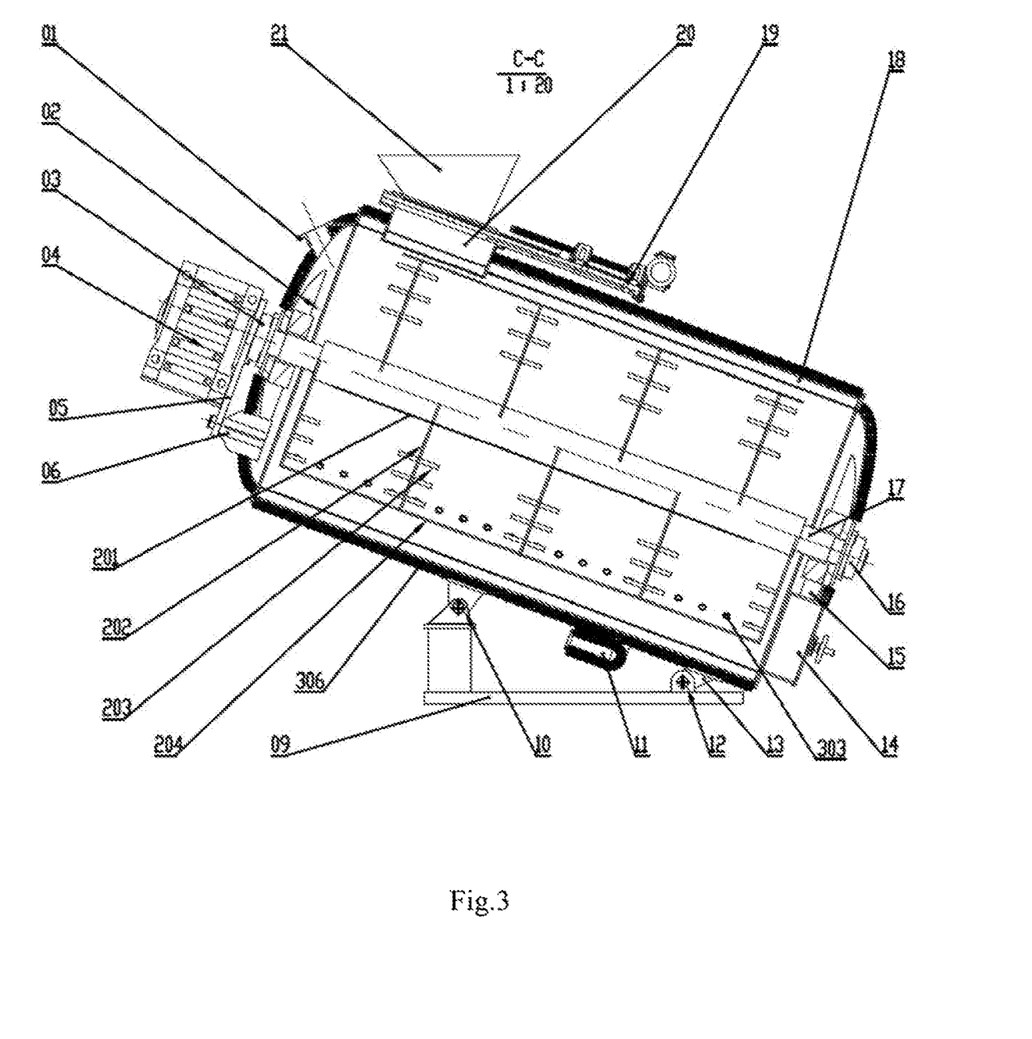
FIG. 3 is a cross-sectional view of the inclined aerobic fermentation reactor along line C-C.
Figure 4:
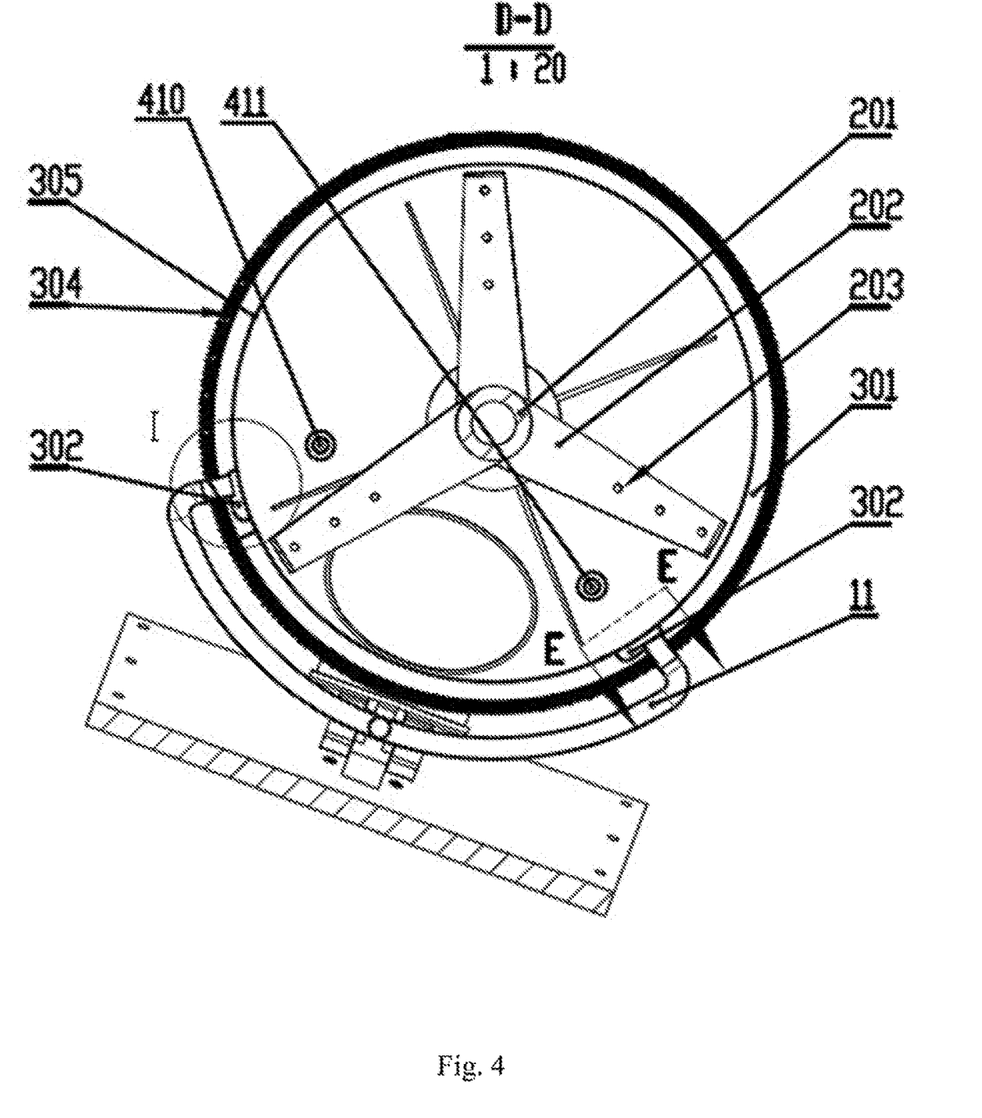
FIG. 4 is a cross-sectional view of the inclined aerobic fermentation reactor along line D-D.
Figure 5:
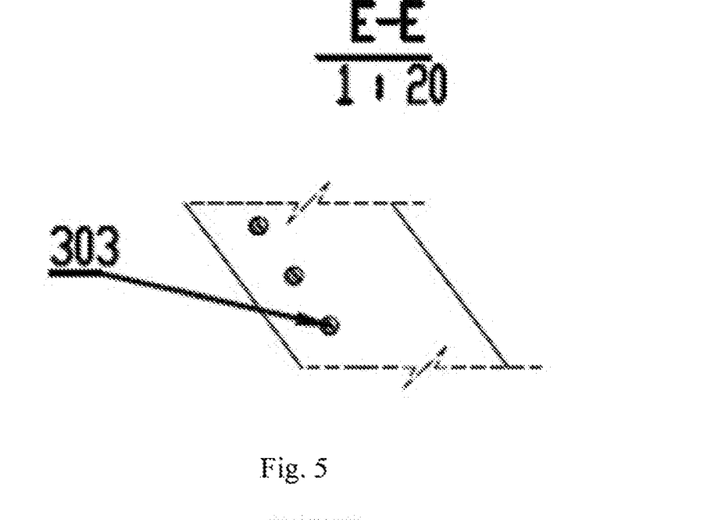
FIG. 5 is a cross-sectional view of the inclined aerobic fermentation reactor along line E-E.
Figure 6:
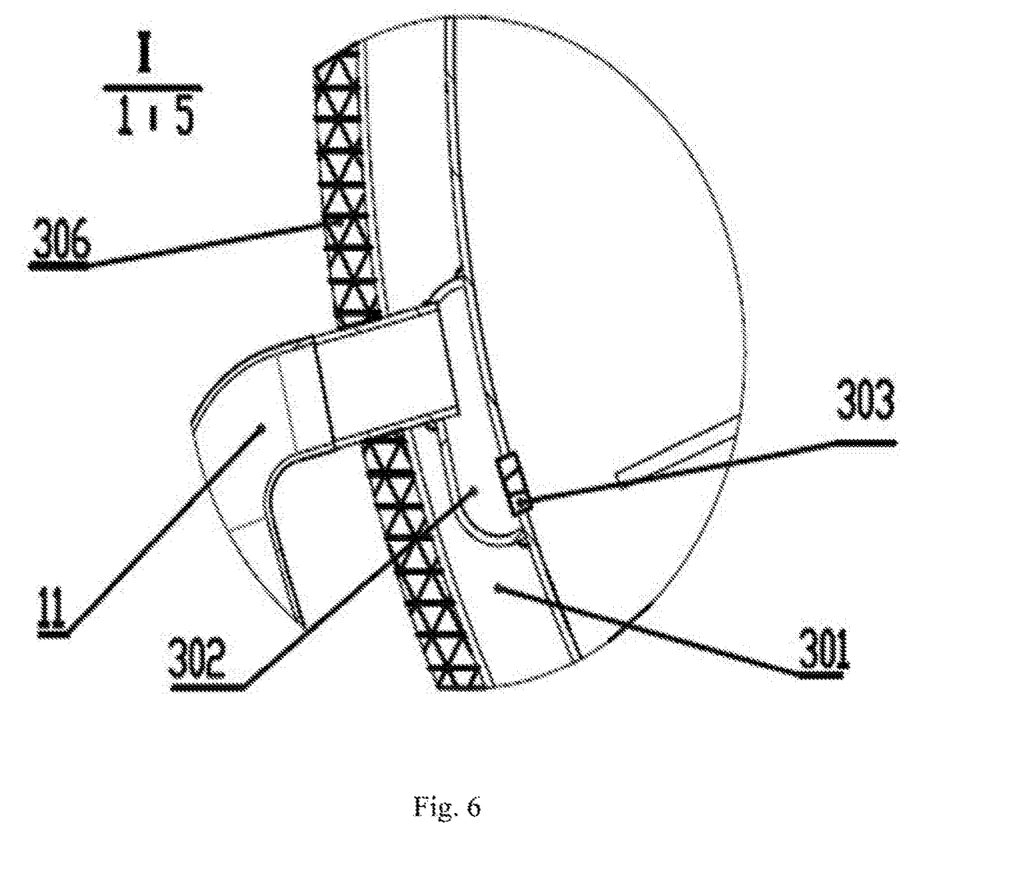
FIG. 6 is an enlarged view of a portion I in FIG. 4.
Figure 7:
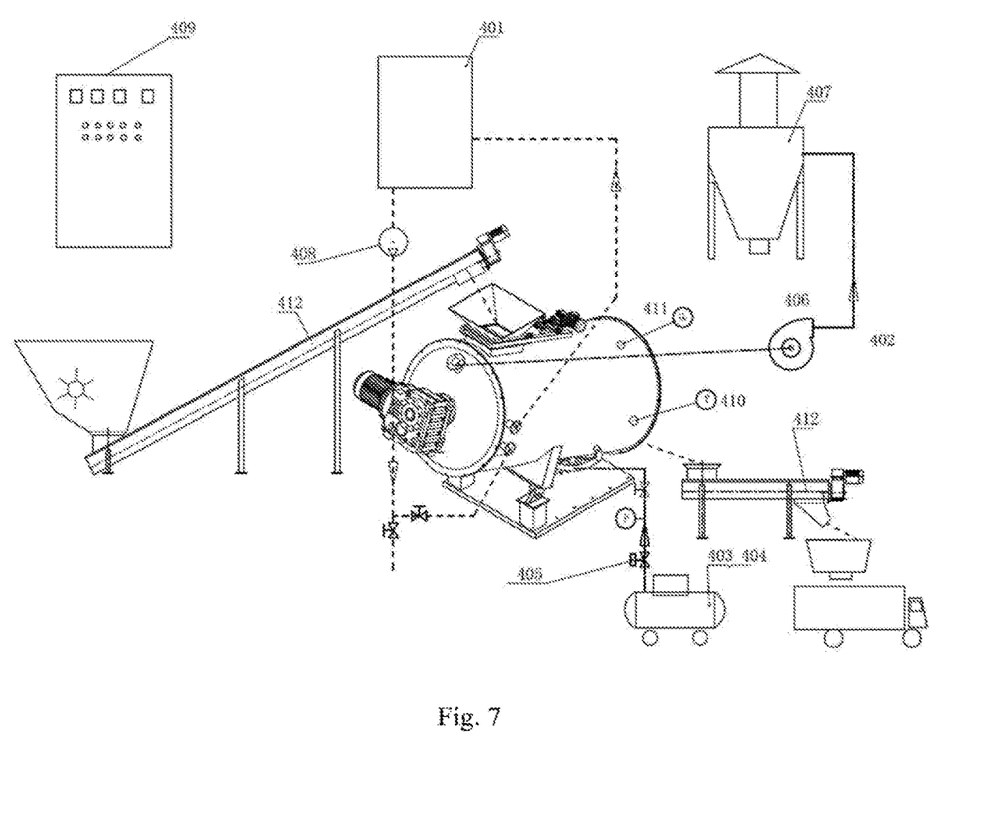
FIG. 7 is a process system diagram of the inclined aerobic fermentation reactor.
Figure 8:
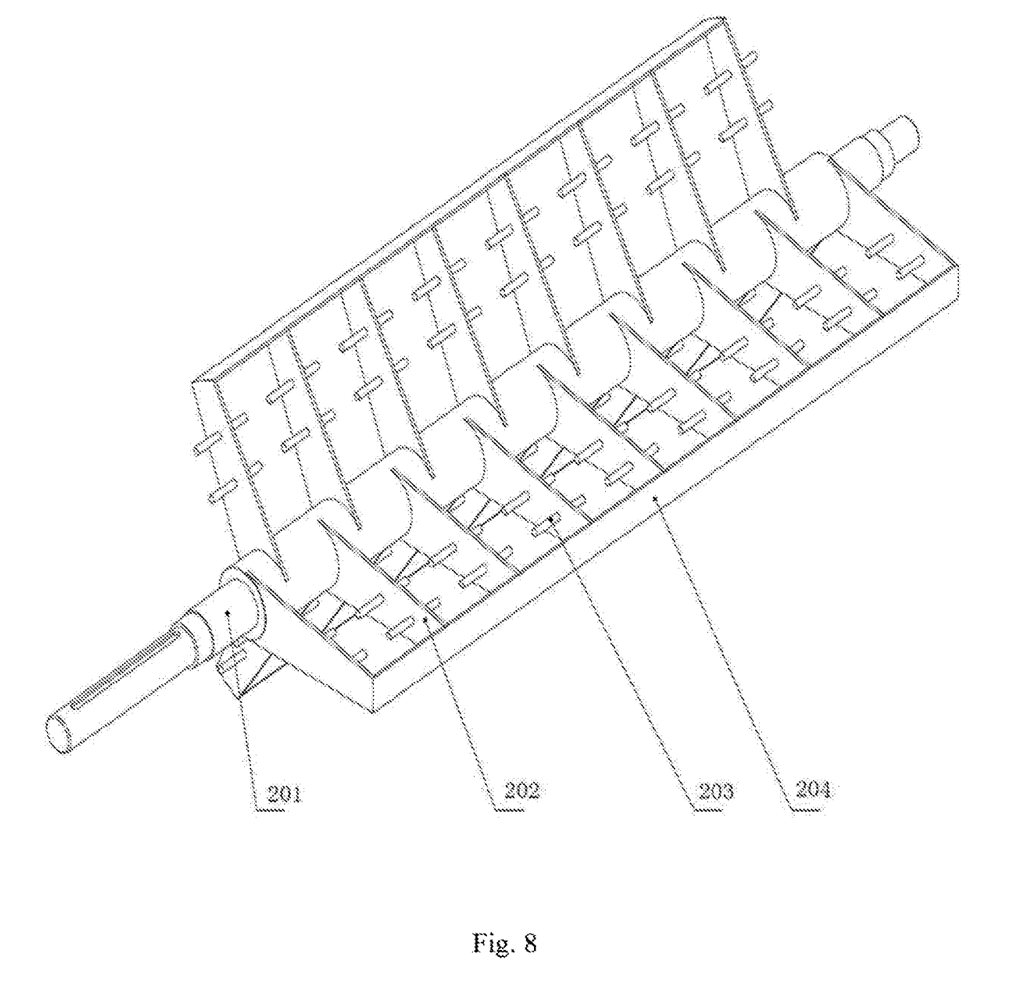
FIG. 8 is a 3D view of an energy-saving stirrer used for wall-sticking fermentation materials.
Figure 9:
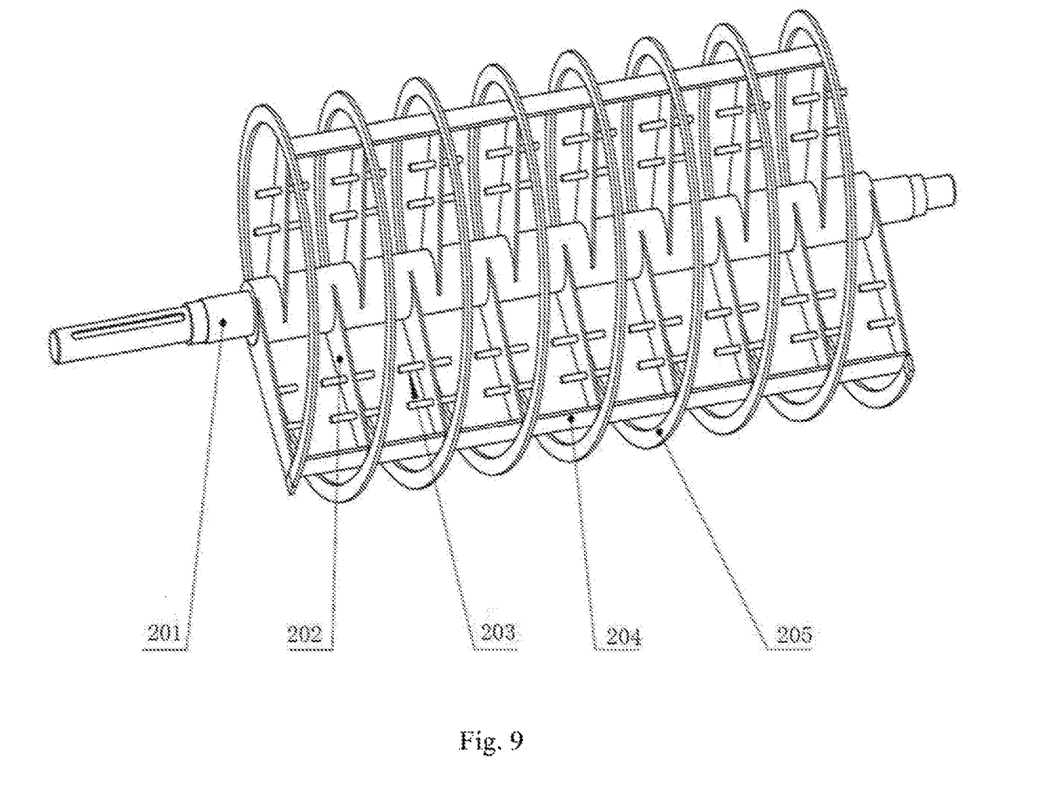
FIG. 9 is a 3D view of an energy-saving stirrer with the functions of wall sticking proof and spiral transmission.

The energy-saving stirrer is provided with two structures. In one structure, the radial rod is fixed to the stirring shaft, the stirring rod is fixed to the radial rod, the tangential plates are fixed to an end of the radial rod, and hence the energy-saving stirrer used for wall-sticking fermentation materials is formed. In the other structure, the radial rod is fixed to the stirring shaft, the stirring rod is fixed to the radial rod, the tangential plates firstly fixed to the spiral combination are then fixed to an end of the radial rod, and hence the energy-saving stirrer with the functions of wall sticking proof and spiral transmission is formed. A distance between the tangential plates or the spiral combination of the tangential plates and an inner wall of the fermenter is in range of 1-5 cm.

The radial rod is in a lamellar structure, lengths of blades in the lamellar structure are the same, and a width of the lamellar structure is significantly greater than a thickness of the lamellar structure. The stirring rod is in a cylindrical shape, cuboid shape or lamellar shape. If the stirring rod is in the cuboid or lamellar shape, a width of the stirring rod is greater than a thickness of the stirring rod. The tangential plates are in a cylindrical shape, cuboid shape or lamellar shape. If the tangential plates are in the cuboid or lamellar shape, a width of each tangential plate is greater than a thickness of the tangential plate.

Another technical solution of the present invention is a method for aerobic fermentation, which comprises:

(1) designing and manufacturing an inclined reactor of bottom gas-inlet type for aerobic fermentation, wherein a fermenter is provided with a circular inner tank, end covers and a jacket; an airtight fermentation space is formed in the fermenter by the inner tank, an upper end cover and a lower end cover, a feed opening and an exhaust outlet are arranged at an upper part of the fermenter, and a discharge opening is arranged at a lower part of the lower end cover of the fermenter; a length of the fermenter is greater than or equal to a diameter of the fermenter; the fermenter is fixed on a base having a height difference and is hence in an inclined state; an energy-saving stirrer is mounted in the fermenter, and the energy-saving stirrer is formed by connecting several groups of tangential plates or a spiral combination of tangential plates, a radial rod, a stirring rod and a stirring shaft; several groups of air chambers are arranged at an external wall at the bottom of the inner tank of the fermenter, the air chambers are arranged inside the jacket, several aeration nozzles are defined on an inner side of each air chamber, and the aeration nozzles are close to the inner tank; the number of the radial rod of the energy-saving stirrer is multiple, a distance between an end of each radial rod and a center of the stirring shaft is the same, and radial rods are radially fixed to the stirring shaft and are uniformly arranged around the stirring shaft; the number of the stirring rod is multiple, and stirring rods are fixed to the radial rods; and the tangential plates or the spiral combination of the tangential plates are fixedly connected to ends of the radial rods; a feed valve is arranged for the feed opening at the upper part of the fermenter; the feed valve comprises a manual valve and an automatic valve; a heat insulating material is wrapped around the fermenter; a heat conductive medium-inlet flange and a heat conductive medium-outlet flange are respectively arranged at a lower part and an upper part of the jacket of the fermenter, and are respectively connected to an inlet and an outlet of heat conductive medium-circulating pipes to form a heat circulating loop; the air chambers are connected to a gas valve and a high-pressure gas source via a gas inlet pipe, the high-pressure gas entering into the air chambers is firstly heated by the heat conductive medium circulated in the jacket, then enters into the fermenter via the aeration nozzles, and is hence thoroughly mixed with materials to be fermented;

(2) starting devices, wherein a main power source is closed to delivery electric power to the devices, start buttons of the devices are pressed, a controller 409 controls to start a high-pressure gas source 403, a circulating pump 408 and a heat source boiler 401 sequentially; a pressure of the high-pressure air is preset according process requirements; heat conductive medium heated by the heat source boiler in a heating system enters into the reactor for aerobic fermentation under the action of the circulating pump 408 via a heat conductive medium-inlet flange 07 so as to heat the inner tank 305 of the reactor for aerobic fermentation;

(3) feeding raw materials, wherein the controller 409 controls to start a transmission device 412, moderate organic wastes under pre-treatment and aerobic bacteria are transmitted into the reactor for aerobic fermentation via the transmission device 412; the controller controls the energy-saving stirrer 17 to rotate when the transmission device 412 starts; after finishing feeding raw materials, the controller controls the transmission device 412 and the energy-saving stirrer 17 to stop, and controls a feed valve 19 to close so as to prevent odor from spilling via the feed opening;

(4) aeration and fermentation, wherein after the feed valve 19 is closed, the controller 409 controls the heating system to heat materials to a preset temperature that is suitable for aerobic fermentation; the controller 409 controls a high-pressure gas source 403/gas valve 405 to start, and controls the energy-saving stirrer 17 to rotate; air from the high-pressure gas source 403 enters into air chambers 302 via a gas inlet pipe 11, and is firstly heated by circulating heat conductive medium in the jacket 304, then enters into the fermenter via aeration nozzles 303, contacts with materials to be fermented and supplies oxygen to the materials;

(5) exhaust gas treatment, wherein when the controller controls the high-pressure gas source 403/gas valve 405 to start, the controller controls an exhaust fan 406 connected to an exhaust outlet to start, the exhaust fan transmits the fermentation exhaust gas to a bio-deodorization filter tower 407 via pipes, and exhaust gas is filtered by the bio-deodorization filter tower 407 before being exhausted;

(6) time-delay controlling, wherein the high-pressure gas source 403/gas valve 405 and the energy-saving stirrer 17 are stopped by adopting time delay; when a preset time delay set by the controller 409 ends, the controller 409 automatically closes the high-pressure gas source 403/gas valve 405, closes the exhaust fan 406 under a time delay, and automatically controls the energy-saving stirrer 17 stop rotating;

(7) automatically adjusting fermentation conditions, wherein the controller 409 controls outputs of the high-pressure gas source 403 according to feedback of an oxygen sensor 411; if the controller determines that oxygen level detected by the oxygen sensor 411 is smaller than a preset lower limit value, the controller controls to open the gas valve 405 and the high-pressure gas source 403, compressed air enters into the fermenter from the aeration nozzles 303 of the air chambers at a bottom of the fermenter via a gas inlet pipe, diffuses upwards, and is thoroughly mixed with materials to be fermented; if the controller determines that the oxygen level detected by the oxygen sensor 411 is greater than a preset upper limit value, the controller 409 controls to close the high-pressure gas source 403; the controller 409 is also capable of setting a timing to open and close the gas valve 405 and the high-pressure gas source 403, and oxygen supplying for fermentation is still ensured without the oxygen sensor 411;

the controller 409 controls the energy-saving stirrer 17 to act according to feedback of a temperature sensor 410; if the controller 409 determines that temperature detected by the temperature sensor 410 is higher than a preset temperature, the controller 409 controls a motor/reducer 04 to start so as to drive the energy-saving stirrer 17 to rotate; stirring time of the energy-saving stirrer 17 is controlled by the controller 409, the controller 409 is also capable of setting a timing to start and stop the motor/reducer 04 so as to turn over the materials periodically;

(8) adjusting temperature of the heating system, wherein the controller 409 controls the circulating pump 408 and heat source boiler 401 to start and stop according to feedback of the temperature sensor 410; if temperature detected by the temperature sensor 410 is lower than a preset value, the circulating pump 408 is started, and the boiler is started after a time delay of t1; if the temperature detected by the temperature sensor 410 is higher than a preset value, the controller 409 controls the heat source boiler 401 stop operating, and controls the circulating pump 408 stop operating after a time delay of t2; values of t1 and t2 are determined by inertia of the system, which can be determined and adjusted in operation site;

(9) discharging materials, wherein when a preset fermentation time ends, the controller 409 controls to open a discharging gate and controls the energy-saving stirrer 17 to reverse so as to discharge materials that have been fermented, and the materials that have been fermented are transmitted to a next procedure via an external transmission device 412;

(10) the controller 409 controlling to close the discharge opening 14 after finishing discharging the materials, the external transmission device 412 being started again to transmit moderate raw materials to be fermented into the inclined reactor of bottom gas-inlet type for aerobic fermentation, and remaining stale acting as yeast to inoculate and ferment raw materials newly added;

(11) repeating above steps so as to ensure bio-fermentation degradation reaction of organic wastes to circulate with a high speed;

(12) after finishing all above steps, the controller 409 switching off power supply of the high-pressure gas source 403 and the heat source boiler, closing the gas valve 405 and the feed valve 19.

I claim:

1. A reactor with an inclined bottom for aerobic fermentation,
wherein a fermenter including a circular inner tank, end covers including an upper end cover and a lower end cover and a jacket;
a fermentation space is formed in the circular inner tank of the fermenter;
a feed opening arranged at an upper part of the fermenter, an exhaust outlet arranged at an upper part of the upper end cover, and a discharge opening is arranged at a lower part of the lower end cover of the fermenter;
a length of the fermenter is greater than or equal to a diameter of the fermenter;
the fermenter is fixed on a base having a height difference and configured to arrange the reactor in an inclined state;
an energy-saving stirrer is mounted in the fermenter, and the energy-saving stirrer including a group of tangential plates, radial rods, stirring rods, a spiral plate and a stirring shaft;
a plurality of air chambers are arranged at an external wall at a bottom of the circular inner tank of the fermenter, a plurality of aeration nozzles are defined on an inner side of each air chamber, and the aeration nozzles are disposed next to the circular inner tank;
wherein, distances between distal ends of the radial rods and a center of the stirring shaft are the same;
the radial rods are radially fixed to the stirring shaft and are uniformly arranged around the stirring shaft;
one or more of the stirring rods are fixed to each of the radial rods;
each tangential plate is fixedly connected to the distal ends of two or more of the radial rods; and
the tangential plates are directly fixedly attached to the spiral plate,
wherein the energy-saving stirrer is configured to stir materials within the fermenter radially and axially and the tangential plates are configured to prevent the materials sticking to an inner wall of the fermenter.

2. The reactor with an inclined bottom for aerobic fermentation according to claim 1, wherein, two ends of the energy-saving stirrer are respectively supported on bearings of the upper end cover and the lower end cover, a motor is mounted at a driving end of the energy-saving stirrer, and the motor drives the energy-saving stirrer to rotate.

3. The reactor with an inclined bottom for aerobic fermentation according to claim 1, wherein, a feed valve is arranged for the feed opening at the upper part of the fermenter; the feed valve comprises a manual valve and an automatic valve; a heat insulating material is wrapped around the fermenter; a heat conductive medium-inlet flange and a heat conductive medium-outlet flange are respectively arranged at a lower part and an upper part of the jacket of the fermenter, and are respectively connected to an inlet and an outlet of heat conductive medium-circulating pipes to form a heat circulating loop.

4. The reactor with an inclined bottom for aerobic fermentation according to claim 1, wherein, said plurality of air chambers are connected to a gas valve and a high-pressure gas source via a gas inlet pipe, the high-pressure gas entering into said plurality of air chambers is firstly heated by the heat conductive medium circulated in the jacket, then enters into the fermenter via the aeration nozzles, and is hence thoroughly mixed with materials to be fermented; the exhaust outlet at the upper part of the upper end cover of the fermenter in the inclined state is connected to an exhaust fan via pipes, the exhaust fan is connected to a bio-deodorization filter tower via the pipes, and exhaust gas is filtered by the bio-deodorization filter tower before being exhausted.

5. The reactor with an inclined bottom for aerobic fermentation according to claim 1, wherein, a temperature sensor and an oxygen sensor are respectively arranged at two ends of the discharge opening of the lower end cover; outputs of the temperature sensor and the oxygen sensor are respectively connected to corresponding inputs of a controller, the controller is configured to compare input values from the sensors with preset values, and outputs of the controller are connected to a circulating pump, a heat source boiler, the energy-saving stirrer, an exhaust fan, a gas valve and a high-pressure gas source; the controller is also capable of setting a preset timing to start and stop the circulating pump, the heat source boiler, the energy-saving stirrer, the exhaust fan, the gas valve and the high-pressure gas source without using the sensors.

6. The reactor with an inclined bottom gas inlet for aerobic fermentation according to claim 1, wherein, a distance between the tangential plates and an inner wall of the fermenter is in range of 1-5 cm.

7. The reactor with an inclined bottom for aerobic fermentation according to claim 1, wherein, each radial rod is in a lamellar structure, lengths of blades in the lamellar structure are the same, a width of the lamellar structure is greater than a thickness of the lamellar structure;

each stirring rod is in a cylindrical shape, cuboid shape or lamellar shape; if the stirring rod is in the cuboid or lamellar shape, a width of the stirring rod is greater than a thickness of the stirring rod;

the tangential plates are in a cylindrical shape, cuboid shape or lamellar shape;

if the tangential plates are in the cuboid or lamellar shape, a width of each tangential plate is greater than a thickness of the tangential plate.

* * * * *